United States Patent
Régnier et al.

(10) Patent No.: US 9,248,271 B2
(45) Date of Patent: Feb. 2, 2016

(54) DETECTION/STIMULATION MICROLEAD WITH ENHANCED POSITIONING

(71) Applicant: SORIN CRM S.A.S., Clamart (FR)

(72) Inventors: Willy Régnier, Longjumeau (FR); Nicolas Shan, Antony (FR)

(73) Assignee: SORIN CRM S.A.S., Clamart (FR)

( * ) Notice: Subject to any disclaimer, the term of this patent is extended or adjusted under 35 U.S.C. 154(b) by 0 days.

(21) Appl. No.: 14/079,298

(22) Filed: Nov. 13, 2013

(65) Prior Publication Data

US 2014/0135883 A1    May 15, 2014

(30) Foreign Application Priority Data

Nov. 14, 2012    (FR) ...................... 12 60840

(51) Int. Cl.
*A61N 1/00* (2006.01)
*A61N 1/05* (2006.01)

(52) U.S. Cl.
CPC . *A61N 1/05* (2013.01); *A61N 1/057* (2013.01)

(58) Field of Classification Search
CPC ............................ A61N 1/0551; A61N 1/0558
USPC ................................................. 607/116, 122
See application file for complete search history.

(56) References Cited

U.S. PATENT DOCUMENTS

| 6,385,492 | B1 | 5/2002 | Ollivier et al. |
| 6,549,812 | B1 | 4/2003 | Smits |
| 2008/0183257 | A1 | 7/2008 | Imran et al. |
| 2010/0010605 | A1 | 1/2010 | Kolberg et al. |
| 2010/0049288 | A1* | 2/2010 | Westlund et al. ............. 607/122 |
| 2010/0114017 | A1 | 5/2010 | Lenker et al. |
| 2011/0071585 | A1 | 3/2011 | Ransbury et al. |
| 2012/0130464 | A1 | 5/2012 | Ollivier |

FOREIGN PATENT DOCUMENTS

| EP | 0 993 840 | 4/2000 |
| EP | 2 455 131 A1 | 5/2012 |
| FR | 2801510 A1 | 6/2001 |

OTHER PUBLICATIONS

Preliminary Search Report for French Patent Application No. 1260840, dated Mar. 1, 2013, 2 pages.

* cited by examiner

*Primary Examiner* — Nicole F Lavert
(74) *Attorney, Agent, or Firm* — Foley & Lardner LLP

(57) ABSTRACT

A microlead includes exposed areas forming stimulation electrodes. The microlead further includes a stimulation zone (ZS) defined by a first preshape of the microcable at the distal end thereof, in a region including the electrodes (30). The microlead further includes a retention zone (ZR) including a retainer shape adapted to abut the wall of the target vessel. The microlead further includes a stretching zone (ZEL) proximal to the retention zone. The stretching zone may be defined by a shape adapted to make the region elastically deformable in the longitudinal direction under the effect of an axial traction/compression stress. The axial traction/compression stiffness in the elongation zone is lower than that in the retention and stimulation areas.

17 Claims, 2 Drawing Sheets

DETECTION/STIMULATION MICROLEAD WITH ENHANCED POSITIONING

CROSS-REFERENCE TO RELATED APPLICATION

This application claims the benefit of and priority to French Patent Application No. 1260840, filed Nov. 14, 2012 (now abandoned), which is incorporated herein by reference in its entirety.

BACKGROUND

The invention relates to "active implantable medical devices" as defined by the Directive 90/385/EEC of 20 Jun. 1990 the Council of the European Communities. This definition may include implants to continuously monitor heart rhythm and deliver, if necessary, electrical stimulation or resynchronization pulses. This invention relates more specifically to cardiac pacing leads to be implanted in the heart coronary network to allow the stimulation of a left or right cavity, a ventricle or an atrium.

Unlike the right cavities, for which implanting endocardial leads via the right peripheral venous system is sufficient, the implantation of permanent leads in a cavity of the left heart involves significant risks, such as the risk of bubbles passing to the cerebral vasculature located downstream of the left ventricle. For this reason, when it is desirable to stimulate a left cavity, it is most often chosen not to introduce a lead into the cavity to pace, but rather in the coronary network, the lead being provided with an electrode that is applied against the epicardial wall of the left ventricle or of the left atrium. These leads thus stimulate the heart muscle via one or more point electrodes whose position is a function of the predefined trajectory of the cannulated vein. A lead of this type is, for example, the Situs LV model marketed by Sorin CRM (Clamart, France) and described in EP 0993840 A1 and its US counterpart U.S. Pat. No. 6,385,492 (Sorin CRM S.A.S., previously known as ELA Medical). The introduction of such a lead is via the coronary sinus, from its opening in the right atrium. The lead is then pushed and oriented along the network of coronary veins to the selected site. This procedure is very difficult due to the particularities of the venous system, including the gradual reduction in diameter of the veins as the lead progresses into the selected coronary vein. Once the target vein is reached, the surgeon is looking for a satisfying stimulation site, with a good electrical contact with the stimulation electrode against the epicardial tissue. Then, contact should be maintained despite various variations or stresses over time.

A recent trend in the pacing of the left ventricle is the reduction of the diameter of the implantable portion in the coronary network, to a diameter of less than 4 French (1.33 mm), or even to less than 2 French (0.33 mm).

The size of the lead body is indeed a factor directly related to the controlled guiding capacity of the lead in the coronary venous system in order to be able to select specific stimulation sites located in certain collateral veins.

A lead is described in EP 2455131 A1 and US 20120130464 (Sorin CRM). It includes a lead body with a hollow sheath in which a microcable having a diameter of about 0.5 to 2 French (0.17 to 0.66 mm) slides. The micro cable can emerge to a length of 1 to 200 mm beyond the outlet of the lead body. This microcable, which forms the active part of the lead, has a plurality of exposed portions forming a succession of individual electrodes. The electrodes together form a network connected in series to increase the stimulation points in a deep area of the coronary network.

Its very small diameter allows the introduction of the microcable in a first vein ("go" vein) and then to a second anastomosis vein ("back" vein) ascending therein. There is a very frequent presence of distal anastomosis in the coronary venous system. In other words, at the end of some veins there can be passage to another vein, with the possibility of communication between two separate veins at the anastomosis via their respective distal ends. It thus becomes possible, with a single lead, to simultaneously stimulate two relatively remote areas located in two separate veins. The double effect of both the distance of the two areas and of the multiplication of points of stimulation in each zone can provide a particularly beneficial effect for the resynchronization of the functioning of the heart.

Another advantage of the small diameter of the active part of the lead is that it avoids the obstruction of a portion of the blood flow in the vein, which would lead to a deficiency of irrigation of the venous system downstream of the lead end.

Reducing the diameter of the lead, however, is not without drawbacks. Indeed, when the diameter of the lead is significantly lower than that in the vein, it can be difficult to ensure continuous contact with the electrodes. The exposed portion of the microcable, which forms an electrode, can be located in an intermediate, "floating" position in the middle of the vein, resulting in the contact points between the microcable and the wall of the vein being made in electrically isolated areas. Moreover, even in case of actual contact between the electrodes and the vein wall, this configuration may not be stable, because of a permanent heartbeat.

This may be particularly true in the case of microcables inserted through an anastomosis. If the veins are of small diameter in the region of the anastomosis, typically less than 1 French (0.33 mm), beyond the anastomosis they may join the coronary sinus after having passed the left ventricle, and the vein diameter increases. The very thin microcable, allowing to cross the anastomosis, may then move into a region of relatively large diameter, resulting in difficulty establishing a stable contact between the electrodes and the wall of the vein in the region.

One problem of the invention is to propose a structure of microlead ensuring continuous contact of all electrodes with the coronary veins, fixing the position of the lead in order to sustain the effectiveness of the stimulation. Another problem is the risk of displacement of the active part of the lead after it was implanted.

EP 2455131 A1 cited above provides for a retaining mechanism, such as a helical relief formed on the end of the lead body near the end thereof, near the outlet where the microcable emerges. The end of the lead body thus has a locally increased diameter of about 7 French (2.33 mm) for the mechanical holding of the lead body into the vein.

FR 2801510 A1 (corresponding to U.S. Pat. No. 6,549,812 B1) describes another mechanism for holding the lead in the target vein. However, this holding mechanism has the disadvantage of large size and may partially block the passage of blood flow in the vein. Moreover, although it can provide good retention of the lead body, it does not protect the portion of the lead inserted into the deep venous system. In such a case the telescopic microcable may be displaced by large movements of the patient. For example when a patient raises his arm, such movement tends to elongate the superior vena cava, with a risk of local traction applied to the lead, which traction is transmitted to the distal region implanted in the coronary network. These movements generated by the human body are thus an additional challenge relating to displacement of electrodes placed on the stimulation area.

SUMMARY

Embodiments of the invention relate to detection/stimulation microleads for implantation in a target vessel, including a vessel of the coronary venous system for the stimulation of a heart cavity. The microlead can include a distal portion formed by an electrically conductive active microcable (e.g., of a diameter at most equal to 2 French (0.66 mm)). The microcable can be coated with an insulation layer. The insulation can include, along said active part and remote from the distal end of the microlead, one or more exposed regions forming stimulation electrode(s), intended to come into contact with a wall of the target vessel. The microlead includes a stimulation zone on the distal end of the microcable, in a region including the electrodes, and a retention zone. The retention zone is configured to abut against the wall of the target vessel.

The microlead can further include a stretching zone, located proximal to the retention zone (e.g., at a distance therefrom of between 5 and 150 mm). The zone is defined by a shaped region of the microlead adapted to render it elastically deformable in the longitudinal direction under the effect of an axial traction/compression stress exerted on the microlead in its proximal region relative to the elongation area. The axial traction/compression stiffness of the elongation area is less than the axial traction/compression stiffness of the retention and stimulation zones.

Thus, the axial forces exerted on the proximal portion of the lead between the stretching zone and a connector mounted at the proximal end of the lead is absorbed by deformation of the stretching area. This deformation of the extension area takes place without displacements of the retention and stimulation areas, consequently without a corresponding change in the positioning of the electrodes.

According to various advantageous embodiments:
The distal active portion is free of internal central lumen;
The stimulation zone is defined by a first curved preshape of the microcable at the distal end thereof;
The length of the stretching zone is, in the free state of the microlead, between 10 and 50 mm and its overall dimensions in the radial direction are in the free state of the microlead, included in a casing of an apparent diameter between 5 and 20 mm;
The axial traction/compression stiffness of the elongation zone is between 1 and 2.5 N/mm$^2$, and that of the retention and stimulation zones is between 2.5 and 5 N/mm$^2$; and
The length of the retention area is in the free state of the microlead, between 10 and 40 mm and its overall dimensions in the radial direction are in the free state of the microlead, included in a casing of an apparent diameter between 10 and 50 mm.

According to an embodiment of the invention, a microlead includes a microcable (14) of a diameter not greater than 2 French (0.66 mm). The microlead includes, in a distal portion, exposed areas (30) forming stimulation electrodes, intended to come into contact with a wall of the target vessel. The microlead further includes a stimulation zone (ZS) defined by a first preshape of the microcable at the distal end thereof, in a region including the electrodes (30). The microlead further includes a retention zone (ZR) including a retainer shape adapted to abut against the wall of the target vessel, and a stretching zone (ZEL) proximal to the retention zone. The stretching zone may be defined by a shape adapted to make the region elastically deformable in the longitudinal direction under the effect of an axial traction/compression stress. The axial traction/compression stiffness in the elongation zone is lower than that in the retention and stimulation areas.

In one embodiment, the elongation zone is defined by a second preshape of the microcable. The retention area and the stimulation area can be combined areas defined by a same region of the microcable. The microcable can advantageously include a layer of shape memory polymer permanently providing the first and second preshapes.

In another embodiment, the microlead further includes a microcatheter of a diameter at most equal to 2 French (0.66 mm), from which the distal portion of the microcable emerges and the elongation zone is defined by a first preshape of the microcatheter. The retention area and the stimulation area may be separate areas, the retention zone being located proximal to the stimulation zone and the retention zone being defined by a second preshape of the microcatheter.

One embodiment of the present disclosure relates to a microlead. The microlead includes a distal portion formed by an active microcable. The microcable further includes a stimulation zone at the distal end of the microcable. The microcable further includes a retention zone including a shape formed to abut the wall of a target vessel. The microcable further includes a stretching zone defined by a shaped region to provide elastic deformability in the longitudinal direction under the effect of an axial tension/compression stress exerted on the microlead. The axial traction/compression stiffness of the stretching zone is less than the axial traction/compression stiffness of the retention and stimulation zones.

Another embodiment of the present disclosure relates to a microlead. The microlead includes a stimulation zone defined by a first preshape of the microlead at a distal end thereof. The stimulation zone includes electrodes. The first preshape forms a part of a retainer zone in which at least two surfaces of the microlead abut the wall of the target vessel. The microlead further includes a stretching zone proximal to the retainer zone defined by a shape which provides elastic deformability in the longitudinal direction under the effect of an axial traction and compression stress. The axial traction/compression stiffness in the stretching zone is lower than that in the retainer and stimulation zones.

DETAILED DESCRIPTION

Figure 1:
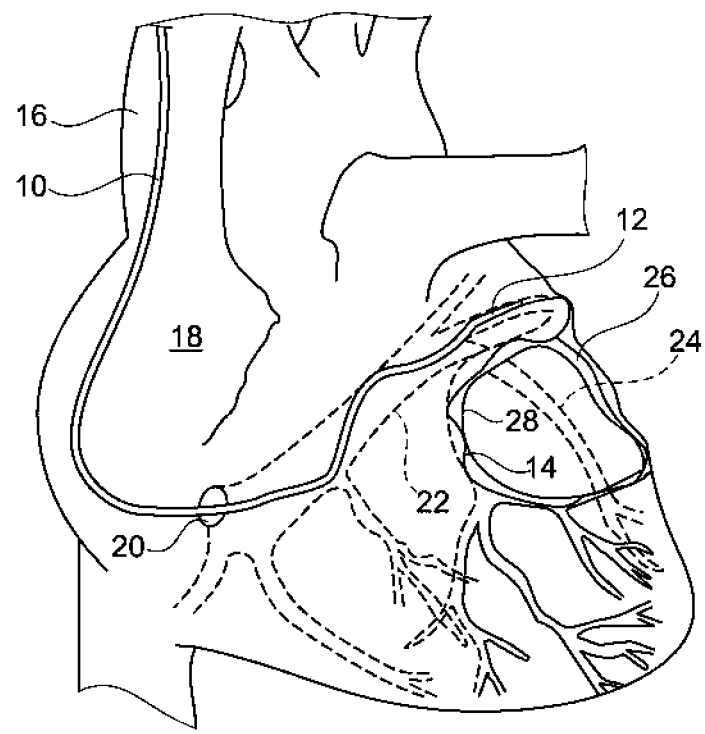
FIG. 1 generally illustrates the myocardium, with the main veins of the coronary network in which a lead according to the invention was introduced for the stimulation of the left ventricle.

FIG. 1 generally illustrates the myocardium and the major vessels of the coronary network, in which a lead 10 to stimulate the left ventricle was introduced. The distal portion of the lead 10, namely the part intended to penetrate into the vessels of the deep coronary network, includes in the illustrated example a microcatheter 12 constituting the distal portion of the lead body. The microcatheter 12 is able to penetrate into the deep network, therefore having a distal portion of very reduced diameter and, furthermore, is intended to be left in place after insertion of the microlead. This microcatheter includes a central lumen housing a microcable 14 of a diameter at most equal to 2 French (0.66 mm), typically about 0.5 to 2 French (0.16 to 0.66 mm), having in its active distal portion a plurality of detection/stimulation electrodes to stimulate the left ventricle from several sites in the coronary vein. Specifically, the lead 10 is shown as endocardially implanted in the coronary venous system via the superior vena cava 16, the right atrium 18 and the input of the venous coronary sinus 20. The coronary venous system then develops into several branches from the great cardiac vein 22, these branches including the posterolateral vein 24, the lateral vein 26 and the anterolateral vein 28.

If necessary, the microlead (that is to say the microcable or the microcable/microcatheter assembly) can reach and cross an anastomosis. An anastomosis is an existing passage at the end of certain veins of the coronary system to another vein, with the possibility of communication between two separate veins at the anastomosis via their respective distal ends. In this case, the microlead is cannulated into a first vein ("go" vein) and then through the anastomosis into a second vein ("return" vein) going up therein, thus placing the active end of microcable in veins of very small diameter. With this configuration, it is possible not only to stimulate the left ventricle from points located deeply in a vein in the coronary network, but also through the anastomosis in the proximal regions of veins in which it would have been difficult to stabilize or set conventional pacing leads of the left ventricle due to the large diameter of the mouth of these veins.

Figure 2:
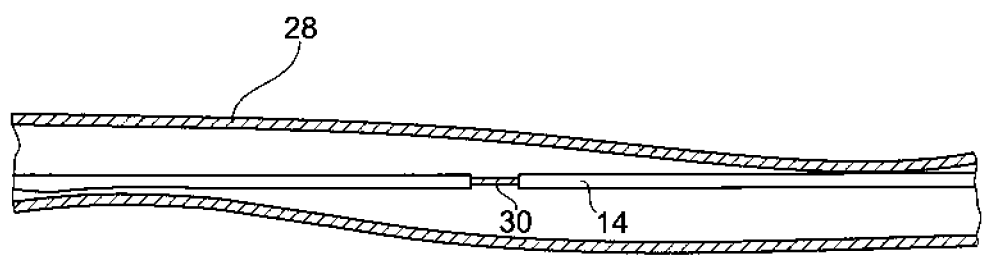
FIG. 2 shows an example of a prior art configuration in which an electrode of a microcable is locally in a region of a relatively large diameter of a vein of the coronary network.

FIG. 2 illustrates the microcatheter 12, with an exposed zone 30 forming an electrode, extending into a vein 28 in a configuration wherein the electrode 30 is not in contact with the wall of the vein. Indeed, one of the difficulties with microcables having a diameter which is very small is to penetrate deep and even, if necessary, to cross through an anastomosis. This can be a disadvantage in a region wherein the vessel is relatively large. In this case, the reduced microcable undermines the stability of the position of the electrode zones, because the cable is "floating" inside the vein, with a significant impact on obtaining a good contact between the electrode and the wall, and thus on the effectiveness of the stimulation.

Figure 3:
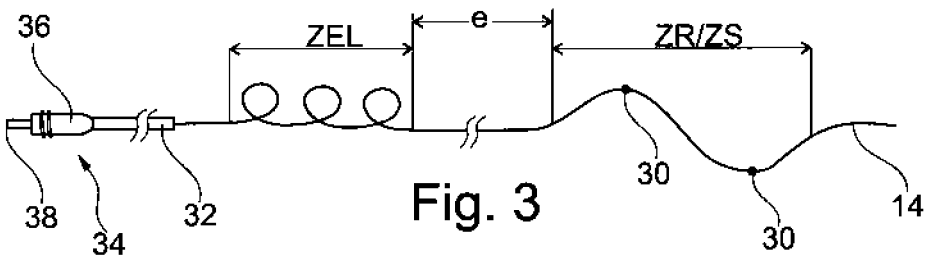
FIG. 3 illustrates a first embodiment of a microlead according to the invention. The embodiment includes a microcable on which a stretching area and a combined retention and stimulation area were formed.

FIG. 3 illustrates an embodiment of the invention. In this illustration, a microcatheter (the hollow lead body) does not go beyond the great cardiac vein 22. The microlead is thus formed by the microcable 14, which in its distal portion emerges from the lead body 32. The microcable 14 runs the length of the lead body 32 to a connector plug 34 which is integral with the body 36 of the lead body 32 and the pin 38 is mechanically and electrically connected to the microcable 14.

The microcable 14 may have a diameter at most equal to 2 French (0.66 mm), typically about 0.5 to 2 French (0.16 to 0.66 mm), and can carry a plurality of sensing/pacing electrodes 30, with a two-or three-dimension preshape, for example in the form of corrugation, to favor the contact of the electrodes with the walls of veins and thus the electrical performance.

The microcable 14 is provided with an insulation coating on its entire length, except for occasionally exposed areas forming the sensing/pacing electrodes. These areas are shown as punctually exposed areas 30 located at the top of both corrugations of the shown preshape.

Regarding the structure of the microcable 14, its core may be a stranded structure wherein each strand is made of nitinol (NiTi alloy) or MP35N-LT (35% Ni, 35% Co, 20% Cr and 10% Mo), materials whose main advantage is their extreme fatigue endurance. This core can be coated with a sheath of platinum-iridium or tantalum (for radiopacity and biostability). Such a structure may meet the requirements of corrosion resistance at the electrodes and endurance against cardiac movements.

The core cable is coated with a thin insulation layer (e.g., of the order of 25 μm thick). The insulation layer can be formed by co-extrusion of the conductor or by heating a heat shrinkable tube. The insulation can be:

A thin layer of parylene (for example of C type): in this case, windows of varying complexity are arranged along the microcable, for example by plasma ablation, to form the electrodes 30; to improve electrical performance, those areas may further be coated, for example, of titanium nitride;

A polyurethane tube interrupted at the locations of electrodes 30; or

One or more layers consisting of tubes of PET (polyethylene terephthalate), fluoropolymer, PMMA (polymethyl methacrylate), PEEK (polyetheretherketone), polyimide or other suitable similar material.

In an exemplary embodiment, the illustrated and described structure results in a very flexible character and floating (floppy) structure of the microcable, in that it provides excellent atraumaticity. Such microcable attacks few tissues and thus preserves the cells in the immediate vicinity of the electrodes.

The microcable is shown as divided into three areas, namely:

A stimulation zone ZS, which is the area supporting the electrodes;

One or more retention zones ZR, whose role is to maintain the lead in place into the vessel, and A stretching area ZEL able to absorb the relative movements caused by the human body; its role is that of a buffer zone preventing any change in the stimulation and retention zones after the lead was implanted.

The retention zones ZR and the stimulation zones ZS may be combined into a combined pacing and retention zone ZR/ZS (as in the case of FIGS. 3 and 4), the retention of the active portion of the lead in the vessel then resulting from the preshape given to the active part or stimulation zone ZS.

In the embodiment of FIG. 3, the elongation zone ZEL includes a corrugation of the microcable 14 in an area located proximally to the combined ZR/ZS stimulation and retention zone, separate from the latter and away therefrom by a distance e.

In the illustrated example, the conformation of the elongation area ZEL is a helical conformation, and the dimensioning of this area and its position relative to the rest of the microlead are chosen so that the elongation area ZEL is in a region of relatively large diameter of coronary arteries, for example in the vicinity of the coronary sinus 20, or even outside of the coronary system, for example, in the superior vena cava 16 or may also be any other vein located between the connector 34 and the proximal end and the retention and stimulation zone ZR/ZS to the distal end.

The gap e between the elongation zone ZEL and the retention and stimulation zone ZR/ZS may thus be between 5 and 150 mm.

The elongation zone may have a length of 10 to 50 mm, and its overall dimensions in the radial direction may be surrounded by a casing of an apparent diameter between 5 and 20 mm (here and in the following, all dimensions are the free state of the microlead, before implantation).

Regarding the combined retention and stimulation zone ZR/ZS, this zone may have a length of 10 to 40 mm, with overall dimensions of the preshape in the radial direction of between 10 and 50 mm (again, in the free state of the microlead).

Stiffness in axial tension/compression of the elongation area ZEL is less than that of the retention and stimulation area ZR/ZS. In other words, the axial force required to deform the stretching zone is less than the force exerted by the retention zone. This configuration can help ensure that there is no movement of the electrodes of the stimulation zone. Thus, even if the patient moves and executes large movements (lifting arm, etc.), the stresses exerted on the proximal part of the lead (between the elongation area ZEL and the connector area 34) are absorbed by deformation of the elongation area ZEL without moving the retention and stimulation areas ZR/ZS, therefore with no effect on the positioning of the electrodes.

The axial traction/compression stiffness in the elongation area ZEL may be between 1 and 2.5 $N/mm^2$, for stiffness in axial traction/compression of the retention and stimulation areas ZR/ZS between 2.5 and 5 $N/mm^2$. These values can be used to make a lead according to the requirements of EN 45502-2-1, which set a maximum allowable tensile force of 5 N on the leads, comparable to an explant situation of the lead.

Figure 4:
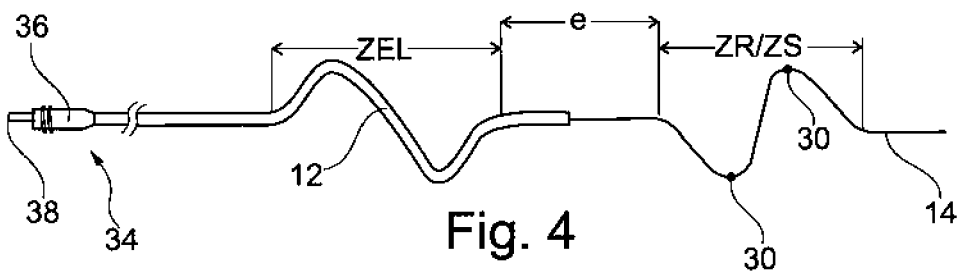
FIG. 4 illustrates a second embodiment of a microlead according to the invention. The embodiment includes a microcable with a combined retention and stimulation area, and an elongation area formed in a region of a microcatheter housing the microcable.

FIG. 4 illustrates another embodiment of the invention, wherein the lead body is terminated at its distal part by a microcatheter 12 from which the microcable 14 emerges. A microcatheter/microcable telescopic assembly is thus available within the coronary system, with possibility of relative axial movement between the microcatheter 12 and the microcable 14 allowing the surgeon to adjust during implantation the emergent length of the distal portion of the microcable.

The microcatheter 12 (which is intended to be left in place after insertion of the microlead) may have a very small diameter (e.g., less than 2 French (0.33 mm)), to penetrate into the deep coronary system. This microcatheter is advantageously made by an extrusion technique with variable speed of two materials with, therein, a tube defining an inner lumen, such as a PTFE tube which receives a coating by extrusion of a material chosen for its properties of flexibility, mechanical strength, resistance to abrasion, ability to be extruded and biocompatibility. The coating material can be for example a polyurethane suitable for long term implantation, or a polyurethane copolymer, a copolymer of polyurethane and silicon, a polyether block amide (such as Pebax for example), or a polyamide. This material can be loaded with a opacifier to X rays ($BaSO_4$ or $TiO_2$ for example) to more easily visualize the microcatheter under fluoroscopy during surgery. A biocompatible coating improving the sliding against the vessel walls, for example a polyvinyl pyrrolidone hydrophilic coating (PVP), or a silicone, may be provided on the outer surface of the microcatheter.

In the embodiment illustrated in FIG. 4, the microlead, which is here formed by the association of the microcable 14 and of the microcatheter 12 includes a stretching area ZEL formed on a preshape of the microcatheter 12, for example a preshape with corrugations, pre-formed by the properties of shape memory of the polyurethane of the microcatheter.

The microcable 14 includes a distal combined retention and stimulation area ZR/ZS comparable to that of the embodiment of FIG. 3. The different dimensions given for the embodiment of FIG. 3 may also be applicable to that of FIG. 4.

Outside of the retention and stimulation areas ZR/ZS, the microcable has a straight shape, merely embracing the curves of the microcatheter 12 particularly in the stretching area ZEL.

Figure 5:
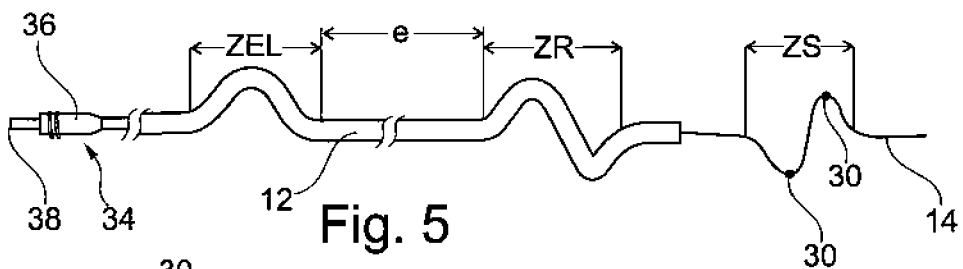
FIG. 5 illustrates another embodiment of a microlead according to the invention. This embodiment includes a microcable on which a stimulation area was formed, and a microcatheter housing that microcable and on which a retention area and a distinct elongation area were formed.

FIG. 5 illustrates another embodiment, which is a variant of the above, wherein the retention area ZR and the stimulation area ZS are distinct. The retention zone ZR is formed on the microcatheter 12, while the stimulation zone ZS is formed on the microcable.

The length of the retention zone ZR may be between 10 and 40 mm, and that of the stimulation zone ZS may be between 20 and 60 mm. Other dimensions may be the same as those given in the example of FIG. 3.

Again, the retention zone ZR of the microcatheter 12 has an axial traction/compression stiffness greater than that of the elongation area ZEL, so that the latter maintains the placement of the retention zone ZR, absorbing the axial stresses to which the proximal portion of the lead is subjected (between the stretching area ZEL and the connector 34).

FIGS. 6-10 illustrate various configurations of two or three dimensional preshapes that can be used for the stretching area ZEL, the retention area ZR and/or the stimulation area ZS.

If these preshapes are used for the stimulation zone ZS, the stimulation electrodes, which are symbolized by the stars 30, may be appropriately placed to ensure contact with the tissues of the vessel. For good electrical performance, it is important that the stimulation electrodes 30 are as close as possible of the tissue to stimulate.

The preshapes can play a dual retention and stimulation role according to the selected configuration, first by creating a contact force for the electrodes on the vein wall, and second by applying a retention force sufficient to block the microcable 14 in the coronary vessel.

Figure 6:
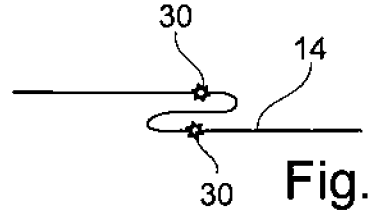
FIGS. 6-10 illustrate various configurations of preshapes used for elongation, retention and/or stimulation zones, of the microlead according to the invention.
Figure 9:
Figure 7:
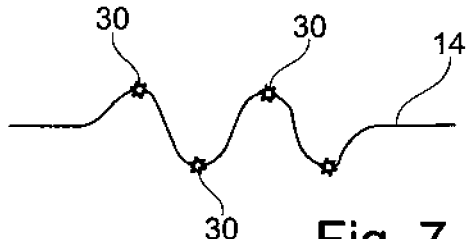
Figure 10:
Figure 8:
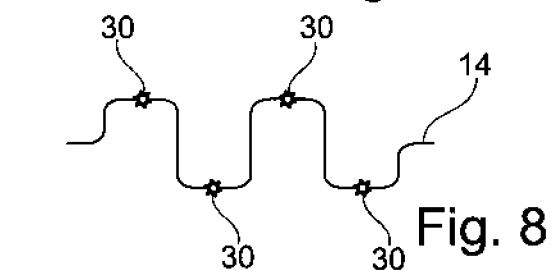

The different configurations shown are all intended to artificially increase the diameter of the implantable system (microcable alone or microcatheter/microcable assembly). It can thus be configured:

In the form of an accordion (FIG. 6);

With a succession of corrugations (FIG. 7), this configuration corresponding to that of FIGS. 3, 4 and 5 for the retention and/or stimulation zones ZR/ZS, and to that of FIG. 5 also for the elongation area ZEL;

In successive slots (FIG. 8);

In the form of an helix (FIG. 9), this configuration corresponding to that of FIG. 3 for the elongation area ZEL. This configuration can also be advantageously applied to the stimulation area ZS, as a result of the helical shape that conforms to the vessel wall in most respects. The electrodes may be located anywhere and they are certainly nearly always in contact with the wall regardless of their location; or In the form of radial-shaped springs (FIG. 10).

In an exemplary embodiment, the elasticity of the microcable the preshapes are sufficiently deformable under radial stress during passage through the coronary veins network such that they do not create any obstacle during implantation.

The invention claimed is:

1. A microlead comprising:
   a distal portion formed by an active microcable;
   a stimulation zone at the distal end of the microcable;
   a retention zone defined by a first shaped region formed to abut the wall of a target vessel; and
   a stretching zone defined by a second shaped region configured to provide elastic deformability in the longitudinal direction under the effect of an axial tension/compression stress exerted on the microlead, wherein the axial traction/compression stiffness of the stretching zone is less than the axial traction/compression stiffness of the retention and stimulation zones.

2. The microlead of claim 1, wherein the stretching zone is positioned to absorb the axial stresses exerted on a portion of the lead between the stretching zone and a connector mounted at the proximal end of the lead.

3. The microlead of claim 2, wherein the deformation occurs without any movement of the retention and stimulation zones and without a corresponding change in the positioning of electrodes of the stimulation zones.

4. The microlead of claim 1, wherein the distal portion extends free of an internal central lumen of a catheter.

5. The microlead of claim 1, wherein the length of the stretching zone is, in a free state of the microlead, between 10 and 50 mm.

6. The microlead of claim 1, wherein the overall dimensions in a radial direction of the stretching zone, in the free state of the microlead, is between 5 and 20 mm.

7. The microlead of claim 1, wherein the axial traction/compression stiffness of the stretching zone is between 1 and 2.5 N/mm2.

8. The microlead of claim 1, wherein the axial traction/compression stiffness of the retention zone and of the stimulation zone is between 2.5 and 5 $N/mm^2$.

9. The microlead of claim 1, wherein the length of the retention zone is, in the free state of the microlead, between 10 and 40 mm.

10. The microlead of claim 1, wherein the overall dimensions in a radial direction of the retention zone are, in the free state of the microlead, between 10 and 50 mm.

11. The microlead of claim 1, wherein the stimulation zone is defined by a first curved preshape of the microcable at the distal end.

12. The microlead of claim 11, wherein the stretching zone is defined by a second preshape of the microcable.

13. The microlead of claim 12, wherein the microcable comprises an outer coating layer of shape memory polymer permanently constituting said first and second preshapes.

14. The microlead of claim 12, wherein the retention zone and the stimulation zone are merged zones defined by a same region of the microcable.

15. The microlead of claim 1, wherein:
   the microlead further comprises a microcatheter from which the distal portion of the microcable emerges, and wherein the stretching zone is defined by a first preshape of the microcatheter.

16. The microlead of claim 15, wherein the retention zone and the stimulation zone are separate zones, the retention zone being located proximal to the stimulation zone, and wherein the retention zone is defined by a second preshape of the microcatheter.

17. The microlead of claim 12, wherein the stimulation zone defined by the first curved preshape and the stretching zone defined by the second preshape of the microcable.

* * * * *